(12) United States Patent
Janik et al.

(10) Patent No.: US 6,788,760 B1
(45) Date of Patent: Sep. 7, 2004

(54) METHODS AND APPARATUS FOR CHARACTERIZING THIN FILMS

(75) Inventors: Gary Janik, Palo Alto, CA (US); Roger Kroeze, Palo Alto, CA (US); Murali Narsimhan, San Jose, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 98 days.

(21) Appl. No.: 10/317,607

(22) Filed: Dec. 11, 2002

Related U.S. Application Data
(60) Provisional application No. 60/368,608, filed on Mar. 28, 2002.

(51) Int. Cl.$^7$ ............................................. G01N 23/223
(52) U.S. Cl. ............................... 378/45; 378/50; 378/83
(58) Field of Search ............................... 378/44–55, 70, 378/82, 83

(56) References Cited

U.S. PATENT DOCUMENTS

| | | | | | |
|---|---|---|---|---|---|
| 4,037,104 A | * | 7/1977 | Allport | ......................... | 378/56 |
| 4,959,848 A | * | 9/1990 | Parobek | ......................... | 378/46 |
| 5,113,421 A | * | 5/1992 | Gignoux et al. | ............... | 378/50 |
| 5,210,414 A | | 5/1993 | Wallace et al. | .............. | 250/307 |
| 6,038,280 A | * | 3/2000 | Rossiger et al. | .............. | 378/50 |
| 6,434,217 B1 | * | 8/2002 | Pickelsimer et al. | ........... | 378/89 |

OTHER PUBLICATIONS

Hombourger et al., *Lexes And Sims As Complementary Techniques For Full Quantitative Characterization Of Nanometer Structures*, pp. 1–4, Cameca, 103 Boulevard Saint–Denis, 92403 Courbevoie, France.

Staub et al., *Shallow Probe: Quantitative Metrology Tool For Thin Film And Shallow Implants*, pp. 1–39, www.cameca.fr.

Cameca Shallow Probe Brochure 2002 "*Analytical Information & Physical Modeling*".

Jean–Louis Pouchou, *X–Ray microanalysis of stratified specimens*, pp. 81–97, © 1993—Elseibver Science Publishers B.V. All rights reserved.

* cited by examiner

Primary Examiner—Edward J. Glick
Assistant Examiner—Jurie Yun
(74) Attorney, Agent, or Firm—Beyer Weaver & Thomas, LLP

(57) ABSTRACT

Methods and apparatus are providing for characterizing thin films in an integrated circuit device. A target including multiple layers is scanned using an x-ray emission inducer. X-ray emissions characteristic of materials in the target are measured. In one example, multiple beam energies are used to conduct the scan. In another example, continuously varying beam energies are used. Information such as K-ratios or the intensity of the x-ray emissions is provided to determine the thickness and/or composition of layers in the scan target.

49 Claims, 8 Drawing Sheets

METHODS AND APPARATUS FOR CHARACTERIZING THIN FILMS

CROSS-REFERENCE TO RELATED APPLICATIONS

This application claims priority under U.S.C. 119(e) from U.S. application No.: 60/368,608 filed Mar. 28, 2002 entitled, "METHODS AND APPARATUS FOR CHARACTERIZING THIN FILMS" by Gary Janik, Roger Kroeze and Murali Narsimhan which is incorporated by reference in its entirety for all purposes. The present application is also related to U.S. patent application Ser. No. 09/990,171 by Mehran Nasser-Ghodsi and Anne Testoni, and titled Methods and Apparatus for Void Characterization and to U.S. patent application Ser. No. 09/990,170 by Mehran Nasser-Ghodsi and Jeffrey Reichert and titled Method and Apparatus for Defect Localization. The present application is also related to U.S. patent application Ser. No. 09/695,726 by Shing Lee, and titled Film Thickness Measurement Using E-Beam Induced X-Ray Microanalysis as of filing on Oct. 23, 2000. All of the above noted applications are incorporated herein by reference for all purposes.

BACKGROUND OF THE INVENTION

1. Field of the Invention

The present invention generally relates to the field of inspection and analysis of specimens. More particularly, the present application relates to characterizing thin films in semiconductor integrated circuits.

2. Description of Related Art

Thin film layers are widely used in semiconductor devices. In one example, a thin film barrier layer is used to prevent copper from migrating into an insulator. However, a variety of factors cause uneven thickness and composition in thin film layers and prevent thin films from effectively performing their functions. Defects can ultimately lead to failure of integrated circuits.

Consequently, it is desirable to provide improved techniques and systems for measuring thin films that more effectively characterize thin film layers in a variety of semiconductor devices.

SUMMARY

Methods and apparatus are provided for characterizing thin films in an integrated circuit device. A target including multiple layers is scanned using an x-ray emission inducer. X-ray emissions characteristic of materials in the target are measured. In one example, multiple beam energies are used to conduct the scan. In another example, continuously varying beam energies are used. Information such as K-ratios or the intensity of the x-ray emissions is provided to determine the thickness and/or composition of layers in the scan target.

According to various embodiments, a method for characterizing thin films is provided. A first scan target in an integrated circuit device is scanned by using a particle beam generator configured to emit particles at a first energy. The particles interact with a first layer comprising a first material and a second layer comprising a second material in the scan target. The second layer lies beneath a first layer. X-ray emissions associated with scanning at the first energy are detected. The first scan target is scanned by using the particle beam generator configured to emit particles at a second energy. The particles interact with the first layer comprising the first material and the second layer comprising the second material in the scan target. X-ray emissions associated with scanning at the second energy are detected. The second layer is characterized by using x-ray emissions from the first and second materials resulting from scans at the first and second energies.

According to other embodiments, an apparatus for measuring thin films is provided. The apparatus includes and x-ray emission inducer and an x-ray emission detector. The x-ray emission inducer is operable to scan a first scan target in an integrated circuit device at a first energy and a second energy. The x-ray emission inducer causes x-ray emissions from a first layer comprising a first material and a second layer comprising a second material in the scan target. The x-ray emission detector is operable to measure characteristic x-ray emissions resulting from the scan at the first energy and the second energy. The x-ray emissions are characteristic of the first and second materials scanned at the first energy and the second energy are measured to characterize the second layer.

According to still other embodiments, a method for measuring thin films is provided. A first scan target in an integrated circuit device is scanned by using an x-ray emission inducer configured to scan at energies continuously varying between a first and a second energy. The scan target includes a first layer comprising a first material and a second layer comprising a second material. X-ray emissions associated with scanning at energies continuously varying between the first and second energies are detected. The x-ray emissions detected include emissions characteristic of the first and second materials used to determine the thickness and composition of the second layer.

In some embodiments, both a first and second layer are characterized. Characterization can include determining the thickness and composition of the various layers.

These and other features and advantages of the present invention will be presented in more detail in the following specification of the invention and the accompanying figures which illustrate by way of example various principles of the invention.

BRIEF DESCRIPTION OF THE DRAWINGS

The invention may best be understood by reference to the following description taken in conjunction with the accompanying drawings. It should be noted that the drawings are illustrative of specific embodiments of the present invention.

DESCRIPTION OF SPECIFIC EMBODIMENTS

The techniques of the present invention allow nondestructive measurement of various layers in a test sample. In one embodiment, the test sample is an integrated circuit having a seed layer, a barrier layer, and a dielectric. During the production of conventional integrated circuits, a defective barrier layer may be inadequate for preventing seepage of seed layer material into a dielectric.

The present invention provides methods and apparatus for measuring thin film layers in integrated circuits. According to various embodiments, the techniques allow a determination of the adequacy of a barrier layer. In one embodiment, an x-ray emission inducer such as an electron beam or an irradiation source is used to scan a test sample. The x-ray emission inducer is configured to scan a target using a variety of different energies. An x-ray detector is aligned near the x-ray emission inducer to detect x-rays emitted from the test sample. According to various embodiments, a material exposed to a scan emits x-rays with emission energies corresponding to the conductive material. For example, copper bombarded by electrons emits x-rays characteristic of copper while tantalum bombarded by electrons emits x-rays characteristic of tantalum. In one example, the scanning of a target with a minimal amount of barrier material may not emit many x-rays characteristics of the barrier material. An x-ray emission detector can measure the intensity of characteristic x-rays emitted at a scan target to determine characteristic thicknesses and compositions of the various layers. According to various embodiments, the composition of particular layers can also be determined.

With information about the thickness of various layers such as a barrier layer, production process can be improved to optimize film conductivity and barrier performance.

Several embodiments of the present invention are described herein in the context of exemplary multilevel integrated circuit structures, including semiconductor structures and overlying metallization or other interconnects, using various levels of conductors that are separated from each other and the substrate by dielectric layers. However, structures formed using other methods of semiconductor fabrication also fall within the scope of the present invention. The techniques of the present invention apply to all surfaces with and without specific layers.

Figure 1:
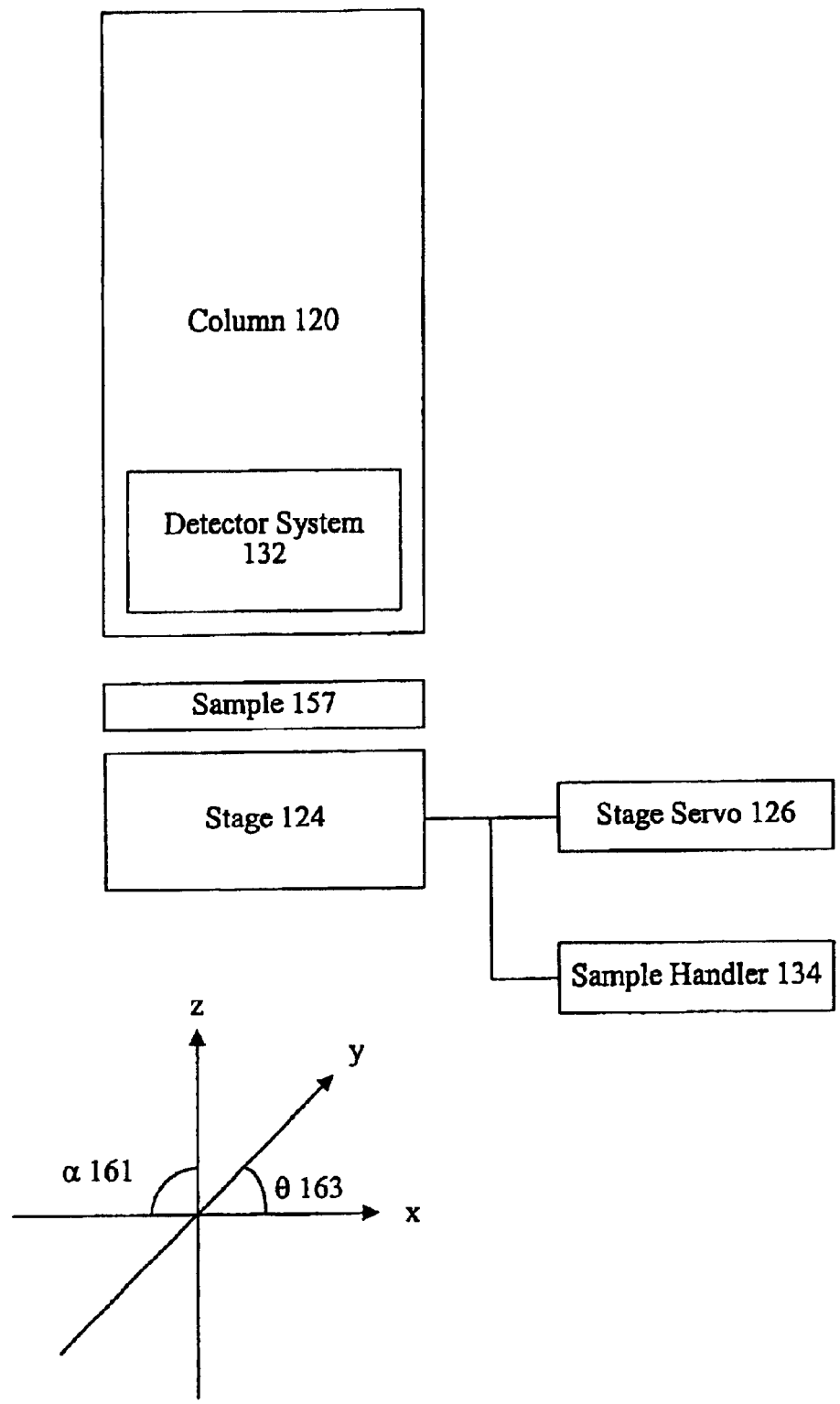
FIG. 1 is a diagrammatic representation of a system that can use the techniques of the present invention.

FIG. 1 is a diagrammatic representation of a system that can use the techniques of the present invention. The detail in FIG. 1 is provided for illustrative purposes. One skilled in the art would understand that variations to the system shown in FIG. 1 fall within the scope of the present invention. For example, FIG. 1 shows the operation of an x-ray emission inducer with a continuously moving stage. However, the test structures and many of the methods described herein are also useful in the context of other testing devices, including x-ray emission inducers operated in step and repeat mode. As an alternative to moving the stage with respect to the emission inducer, the inducer may be moved by deflecting the field of view with an electromagnetic lens. Alternatively, the x-ray emission inducer column and its x-ray detectors can be moved with respect to the stage.

Sample 157 can be secured automatically beneath an x-ray emission inducer 120. Any apparatus that is capable of causing a test sample to emit x-rays is referred to herein as an x-ray emission inducer. According to various embodiments, the x-ray emission inducer 120 is a particle beam generator such as an electron beam generator or an irradiation source such as an x-ray emitter. The sample handler 134 is configured to automatically orient the sample on stage 124. In one embodiment, the stage 124 is configured to have six degrees of freedom including movement and rotation along the x-axis, y-axis, and z-axis. In one embodiment, the stage 124 is aligned relative to the x-ray emission inducer 120 so that the x-directional motion of the stage corresponds to the axis determined by the size of a target. For example, the sample 157 can be aligned so that the x-directional movement of the stage corresponds to the length of a target as viewed from the top of the sample. Furthermore, the sample can be tilted relative to the inducer 120 along the axis determined by the length of the target. Similarly, the sample 157 can also be aligned so that the x-directional movement of stage corresponds to the size of a target. The sample can be tilted relative to the electron beam along the axis determined by the size of the target.

In one example, the stage lies on the x-y plane and the stage is tilted by varying the angle α 161. It should be noted that tilting the sample relative to the inducer 120 can involve tilting the stage, moving the column, or deflecting the beam with a lens. It should also be noted that tilting the stage may involve varying the angle α 161 as well as rotating the stage along angle θ 163. Tilting the sample is one way of allowing scanning from different directions. Where the inducer 120 is an electron beam, the sample can be aligned so that electrons can impinge a scan target from a wide variety of different angles.

Fine alignment of the sample can be achieved automatically or with the assistance of a system operator. The position and movement of stage 124 during the analysis of sample 157 can be controlled by stage servo 126. While the stage 124 is moving in the x-direction, the inducer 120 can be repeatedly deflected back and forth in the y-direction. According to various embodiments, the inducer 120 is moving back and forth at approximately 100 kHz.

According to various embodiments, an x-ray emission detector 132 is aligned alongside the x-ray emission inducer 120 at a 35 degree angle on the z-axis. It should be noted that a close arrangement of inducer 120 and detector 132 allows more accurate detection of x-ray emissions. According to various embodiments, three to six x-ray emission detectors are provided. Each detector is tuned to measure x-ray emissions of a particular layer of material. The inducer 120 and detector 132 as well as other elements such as the stage can be controlled using a variety of processors, storage elements, and input and output devices.

Figure 2:
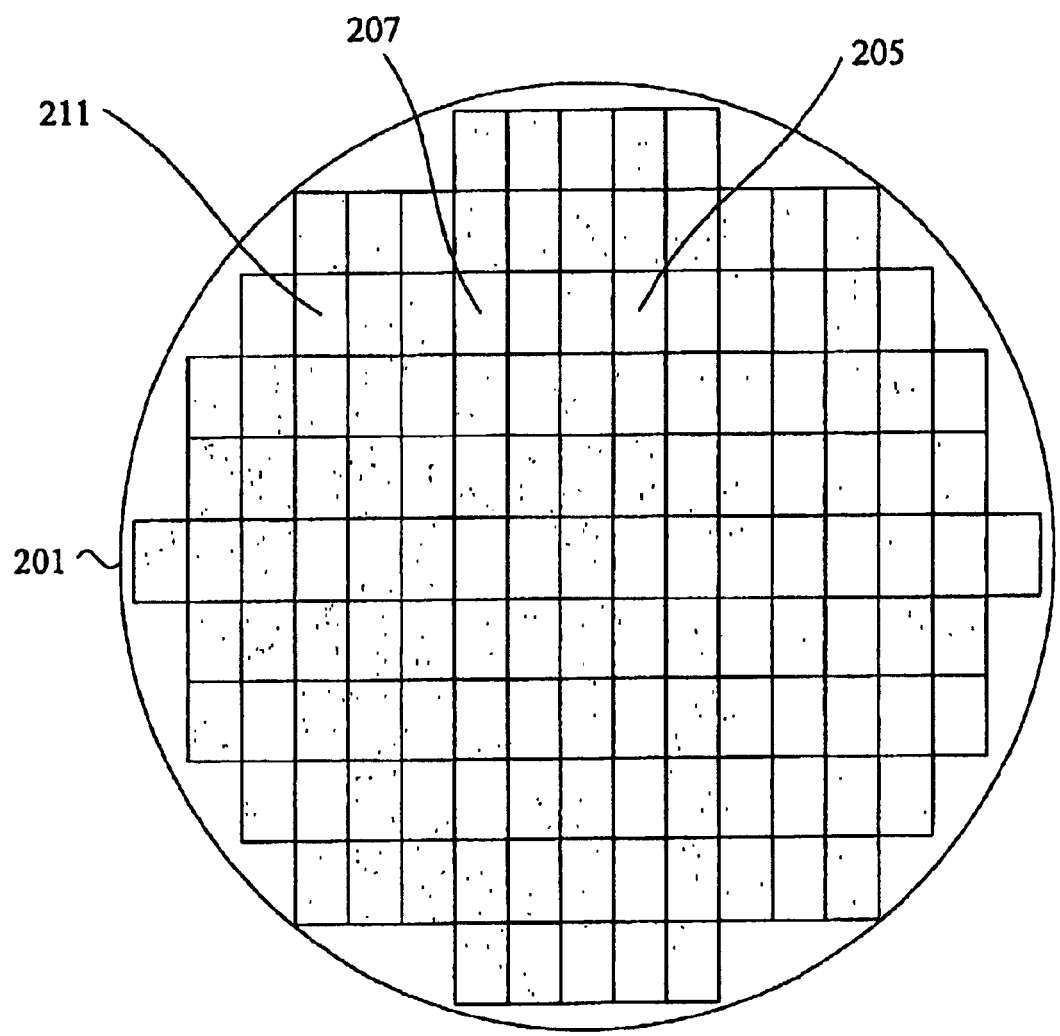
FIG. 2 is a diagrammatic representation of a wafer that may be the sample under test.

FIG. 2 is a diagrammatic representation of a wafer that may be a sample under test. A wafer 201 comprises a plurality of dies 205, 207, and 211. According to various embodiments, the techniques of the present invention for thin film measurement are performed after a metallization or thin film layer is deposited onto a wafer. According to other embodiments, the techniques of the present invention for thin film measurement are performed after several metallization or thin film layers are deposited onto a wafer.

The side of the wafer where the metallization process is performed is herein referred as the top surface of the wafer. The wafer can be scanned to determine the thickness and composition of a top layer and an underlying barrier layer after a thin film or metallization layer comprising a material such as copper is deposited onto the top surface of the wafer. The ability to measure layer thickness and composition during the manufacturing process allows immediate modification of the manufacturing process.

The test methodologies of the present invention can be used as part of an advanced process control system, in which data from the testing process is provided to automated control systems for improving process yield. As an example, the techniques for measuring thicknesses can provide data to automated control systems that dynamically improve the metallization processes.

Figure 3:
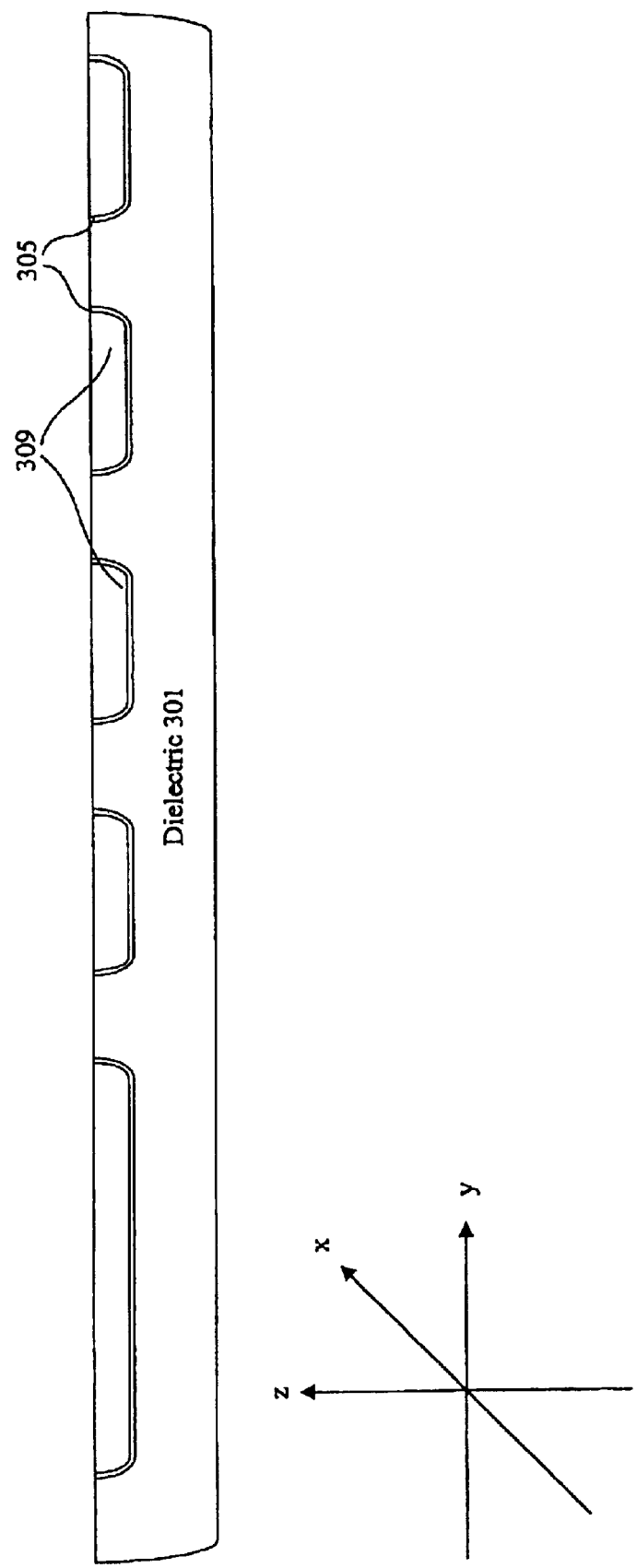
FIG. 3 is a cross-sectional representation showing a plurality of layers.

FIG. 3 is a diagrammatic representation of a cross-section of a test sample. The metallization or thin film layer 309 is deposited on top of a barrier layer 305. According to various embodiments, the thin film layer 309 comprises a material such as copper (Cu) or aluminum (Al) and the barrier layer comprises a material such as tantalum (Ta) or tantalum nitride (TaN). Typically, the metallization or thin film layer 309 is much thicker than the barrier layer 305. A tantalum barrier layer 305 is typically used to prevent copper from thin film layer 309 from seeping into the dielectric 301. In one embodiment, the thin film layer is 100 nm while the barrier layer is 15 nm. According to various embodiments, the techniques of the present invention are used to determine the thicknesses of the thin film layer 309 and the barrier layer 305. In one embodiment, only the thickness of the barrier layer 305 is measured.

According to various embodiments, thickness is measured after a metallization layer 309 is deposited onto a barrier layer 305. The energy of the scan by an x-ray emission inducer such as an electron beam is varied based on the nominal thickness of the thin film layer. The electron beam energy is varied to generate the maximum x-ray emission intensity from the first surface of the sample. If the electron beam energy is insufficient, few electrons will penetrate the surface of the sample and interact with the conductive material, such as copper, to emit x-rays with energy levels characteristic of copper. As will be appreciated by one of skill in the art, electrons interacting with a conductive material such as copper emit K-line x-rays. Characteristic x-rays will be described further below.

If the electron beam energy is too high, many electrons will penetrate the conductive material completely and interact with an underlying barrier or dielectric material. X-rays may still be emitted due to interaction with a barrier or material such as tantalum, however the energy levels of the emitted x-rays will be characteristic of tantalum and not of copper.

According to various embodiments, multiple beam energies are used to scan the target. Scanning a single target with multiple beam energies provides more information for determining the thickness of various layers. In one embodiment, the beam energy between two levels is varied continuously and the intensity of the characteristic x-ray emissions are measured continuously. The selected beam energies used to scan the target may be selected by using a variety of factors such as the expected thicknesses of the various layers.

According to various embodiments, the techniques to the present invention can be used not only to measure the thickness of various layers but also to measure composition. For example, the techniques of the present invention can be used to determine the amount of tantalum and the amount of nitrogen in a tantalum nitride layer. In one embodiment, the thickness of a seed layer and the thickness and composition of a barrier layer can be determined.

Figure 4:
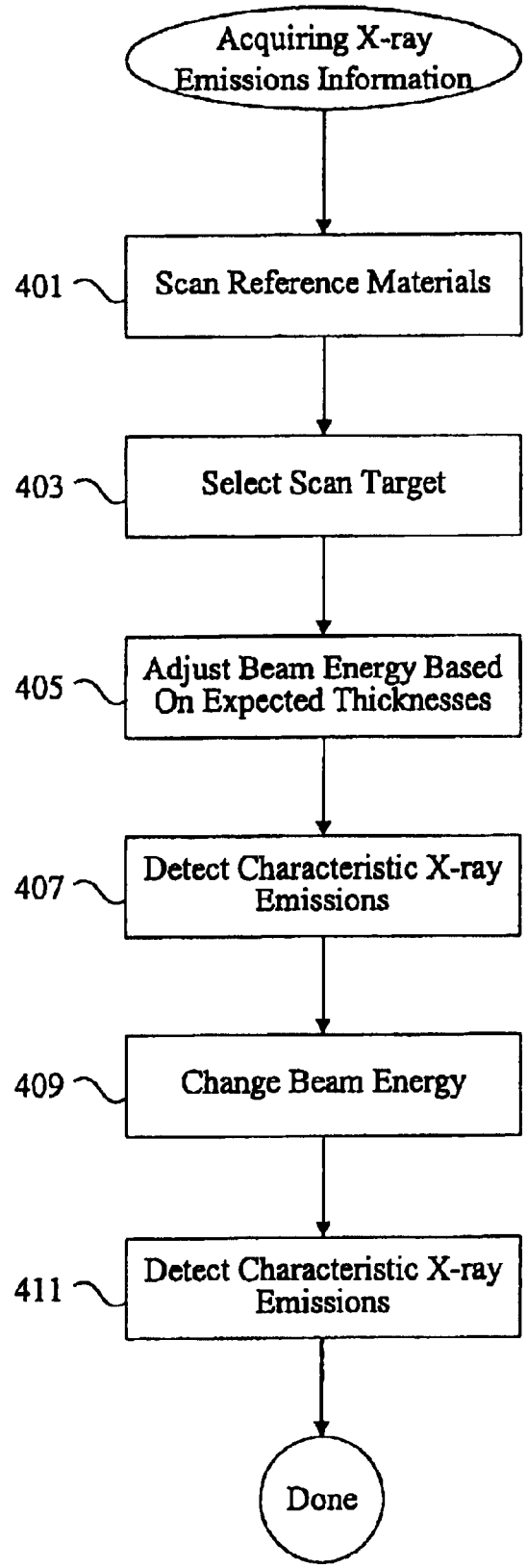
FIG. 4 is a process flow diagram showing the scanning of a sample.

FIG. 4 is a process flow diagram showing one example of a technique for acquiring x-ray emission intensity levels for determining thickness and composition of thin film layers. At 401, reference materials are scanned. In one example, a block of copper, a block of tantalum, and a block containing a compound including nitrogen, such as boron nitride (BN) is scanned in order to determine x-ray emission intensity levels and to calibrate the detection system. The normalization and calibration is performed also to determine k-ratios. At 403, a scan target is selected. In one example, and target is a particular location on a semiconductor device. At 405, the beam energy is adjusted based on the expected thicknesses of the various layers in the target. In one example, the beam energy is adjusted to 20 keV for a copper thin film layer expected thickness of 100 nm and a tantalum nitride barrier layer expected thickness of 15 nm.

According to various embodiments, the target is scanned for approximately one second, although times may vary based on factors such as materials and detection equipment. At 407, x-rays characteristic of copper, tantalum, and nitrogen are detected using detectors tuned to specific wavelengths. At 409, the beam energy is adjusted to a value such as 10 keV for the expected thicknesses noted above. At 411, x-rays characteristic of the materials in a scan target are detected using detectors tuned to specific wavelengths. According to various embodiments, the x-ray emission intensities for the different energy levels can be compared to control x-ray emission intensity measurements to determining thicknesses and compositions for the various layers.

Figure 5:
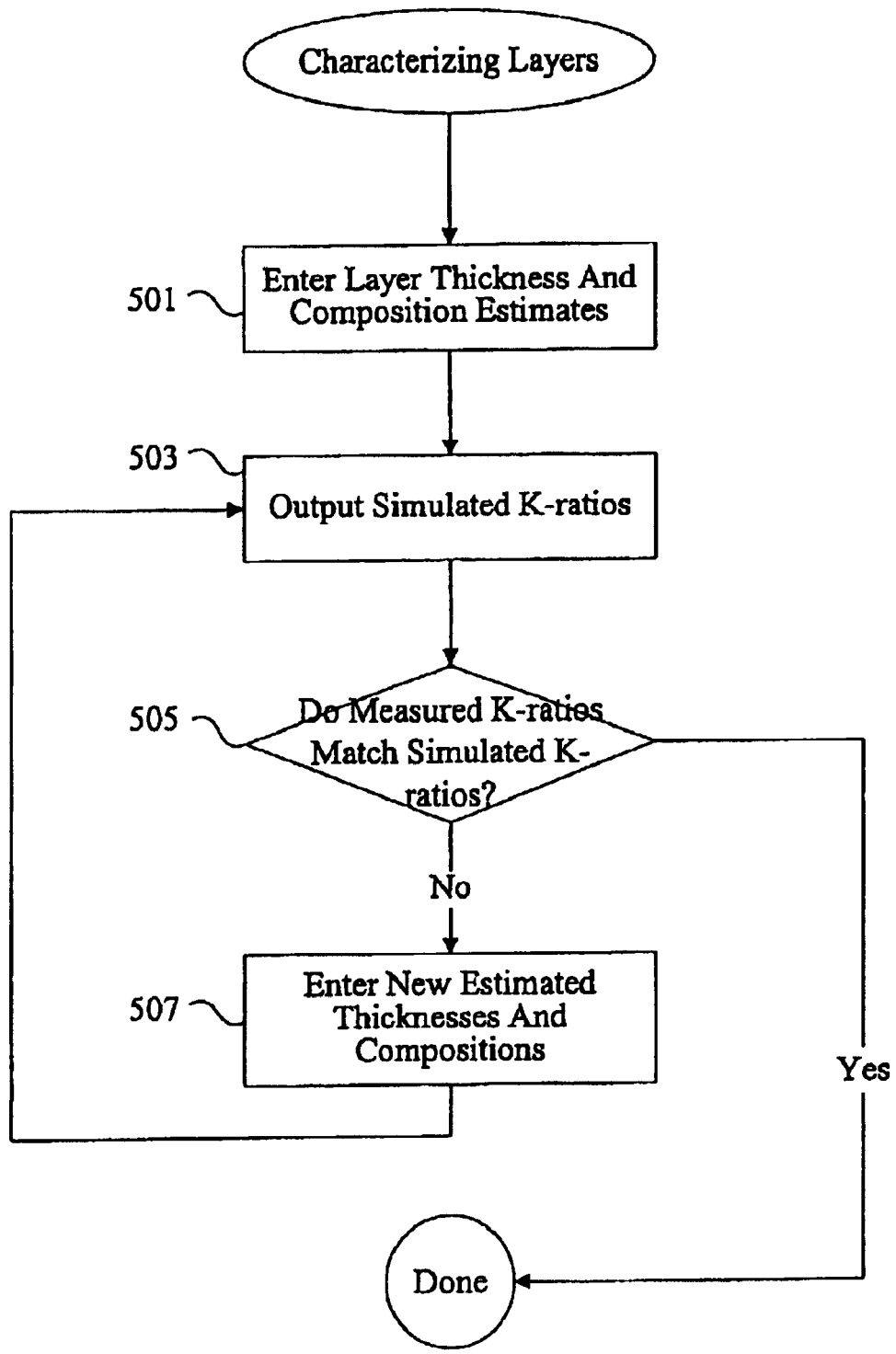
FIG. 5 is a process flow diagram showing the determination of layer thicknesses and compositions.

In one embodiment, the beam energy level is continuously varied and the x-ray emission intensities are continuously measured to provide a large number of data points for determining thicknesses and composition. The x-ray emission intensities resulting from scans at multiple beam energies can be entered into an algorithm such as a regression algorithm. FIG. 5 is one example of a regression algorithm.

At 501, estimates for the thicknesses of the films in an integrated circuit and estimates for the composition of the films are entered into a simulation. In one example, an estimate of 100 nm for a copper layer and an estimate of 40 nm for a tantalum nitride layer are provided. A composition estimate of 1:1 between the tantalum and the nitrogen is also entered. At 503, the K-ratios for each element are output using the simulation based on the energies used in the actual measurement. If the K-ratios measured match the K-ratios simulated for each energy, then the estimates for thicknesses and composition are likely accurate.

In one example, if the measured K-ratios for a copper seed layer match the simulated K-ratios for the copper seed layer, then the copper seed layer is as thick as was estimated. However, if the K-ratio is higher, then the copper seed layer may be thicker than expected. K-ratios here represent the intensity of the x-ray emissions resulting from a scan of a copper seed layer divided by the intensity of the x-ray emissions resulting from a scan of a block of copper. If the K-ratio approaches one, it is likely that the copper is thick enough to simulate a block of copper scan at a particular energy. If the K-ratio approaches zero, it is likely that the copper is very thin and very few x-ray emissions are resulting from the scan.

If the K-ratios do not match at 505, the regression algorithm can enter new estimates of composition and thickness at 507. It should be noted that determining the thickness and composition of a single layer can be substantially simpler than determining the thickness and composition of a barrier layer underlying a seed layer. In one example, if the x-ray emissions characteristic of tantalum are very high, the K-ratio for tantalum would approach 1, thus indicating that a tantalum layer was thick enough to approximate a block of tantalum. However, if the x-ray emissions characteristic of tantalum are low, it may mean that either the tantalum layer is very thin or the copper layer above it is so thick that few x-rays are penetrating the copper layer. Consequently, it is desirable to scan with a range of energies. Furthermore, it is relatively difficult for a beam to penetrate a material such as copper and consequently more K-ratios are needed.

In another example, the K-ratios measured are simply compared to sets of K-ratios for samples with thin film layers of known thicknesses. A database including a wide variety of K-ratio sets for control test samples can be compiled. In one example, the K-ratios for a sample having a copper layer of thickness A and a tantalum layer of thickness B are compiled for a variety of energy levels. K-ratios for different samples having copper and tantalum layers of different thicknesses are also compiled. An algorithm can determine thicknesses based on measured K-ratios simply by comparing the K-ratios to K-ratios in a control database. A database having K-ratios and/or composition information for samples with known layer thicknesses is referred to herein as a K-ratio control database.

Yet another algorithm that can be used is described in X-ray Microanalysis Of Stratified Specimens, by Jean-Louis Pouchou, Analytica Chemica Acta 283, (1993), 81–97, the entirety of which is incorporated by reference for all purposes.

In addition, specific beam energies are more effective in inducing x-ray emissions from particular materials. For example, nitrogen is more excitable by lower energy electrons whereas tantalum is more excitable by higher energy electrons. According to various embodiments, nitrogen is present in a barrier layer beneath a copper seed layer. Although nitrogen is more excitable using lower energy electrons, the electrons used to scan a target containing nitrogen are emitted using a higher energy because lower energy electrons may fail to penetrate a copper seed layer.

The techniques of the present invention allow the characterization of thin film layers. It should be noted that the techniques can be used in conjunction with other techniques to confirm measurements and compositions.

Figure 6:
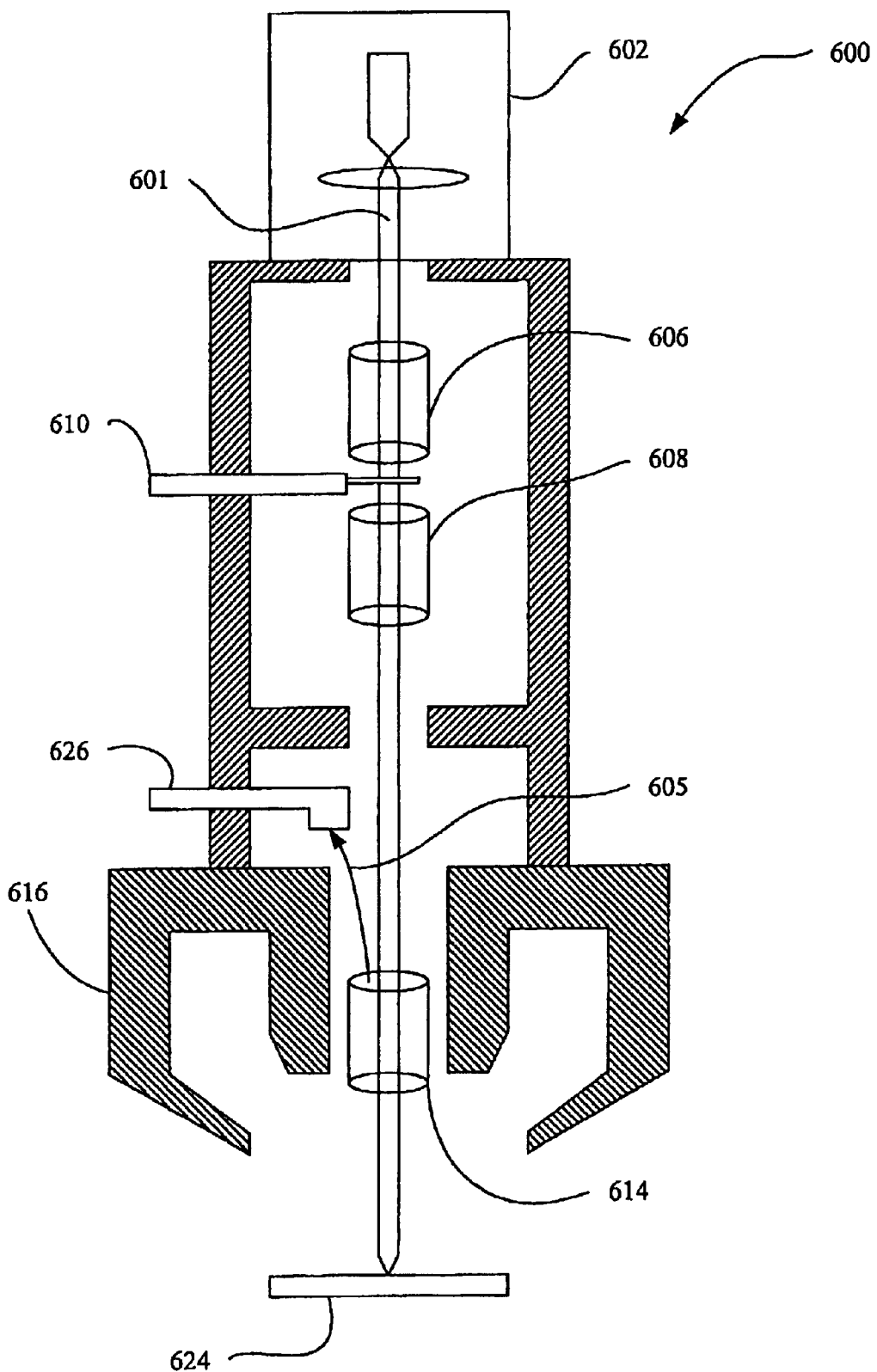
FIG. 6 is a diagrammatic representation of an electron beam that can be used to implement scanning of a sample.

An x-ray emission inducer may be anything that causes x-rays to emanate from the sample under test. In one embodiment, the x-ray emission inducer can be a scanning electron microscope (SEM). FIG. 6 is a diagrammatic representation of a scanning electron microscope (SEM) 600. As shown, the SEM system 600 includes an electron beam generator (602 through 616) that generates and directs an electron beam 601 substantially toward an area of interest on a specimen 624.

In one embodiment, the electron beam generator can include an electron source unit 602, an alignment octupole 606, an electrostatic predeflector 608, a variable aperture 610, a wien filter 614, and a magnetic objective lens 616. The source unit 602 may be implemented in any suitable form for generating and emitting electrons. For example, the source unit 602 may be in the form of a filament that is heated such that electrons within the filament are excited and emitted from the filament. The octupole 606 is configured to align the beam after a particular gun lens voltage is selected. In other words, the beam may have to be moved such that it is realigned with respect to the aperture 610.

The aperture 610 forms a hole through which the beam is directed. The lower quadrupole 608 may be included to compensate for mechanical alignment discrepancies. That is, the lower quadrupole 608 is used to adjust the alignment of the beam with respect to any misaligned through-holes of the SEM through which the beam must travel. The magnetic objective lens 616 provides a mechanism for fine focusing of the beam on the sample.

Figure 7:
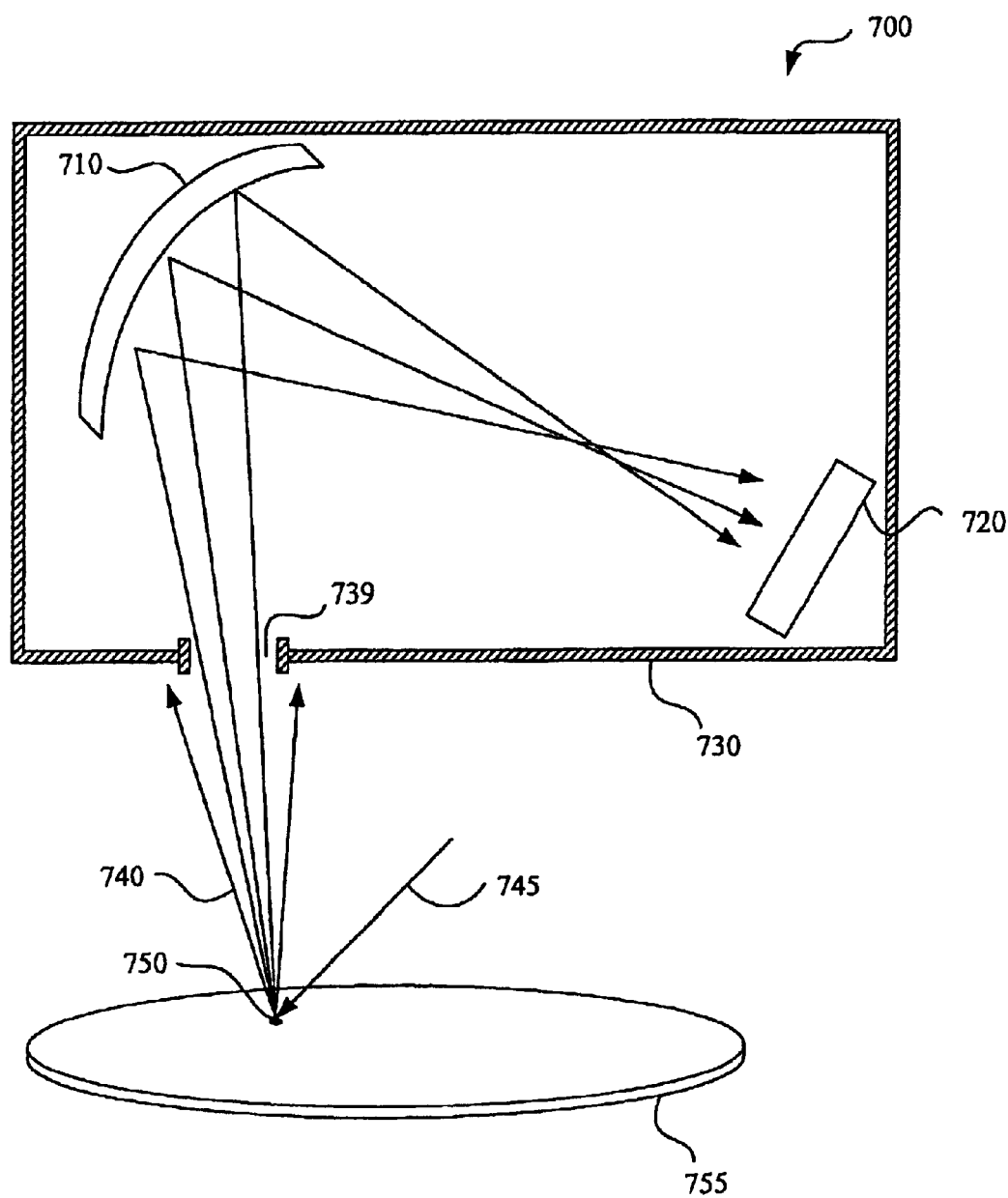
FIG. 7 is a diagrammatic representation of a detector that can be used to measure x-ray emissions.

Any suitable detector for measuring x-rays may be used to detect x-rays emitted from the sample. In one example, three detectors are tuned to individually measure the intensities of Cu, T, and N emissions. FIG. 7 is a cross-sectional representation of a wavelength dispersive system (WDS) x-ray detector in accordance with one embodiment of the present invention. Each x-ray detector 700 includes a housing 730 is having an aperture 739. The housing and aperture are optional for practicing the techniques of the present invention. An electron beam 745 is directed to a focus point 750 on a thin film device 755 (i.e., a semiconductor wafer). The electron beam 745 causes photons 740 to emanate from the focus point 750. The aperture 739 permits a limited amount of photons 740 to enter each detector 700. Upon entering the detector 700, each photon travels along a path to a concave reflective surface 710. The reflective surface 710 directs a portion of photons to a sensor 720. The reflective surface 710 is designed and positioned so that only photons with a specific energy are directed to the sensor 720. The reflective surface 710 may be positioned to direct only photons with an energy characteristic of a certain material to facilitate a film characterization process. By detecting photons of only a specific energy level, detector 700 is capable of obtaining high signal to noise ratios. It should be noted that the reflective surface may be a Bragg reflector or a crystal capable of directing photons towards the sensor.

Figure 8:
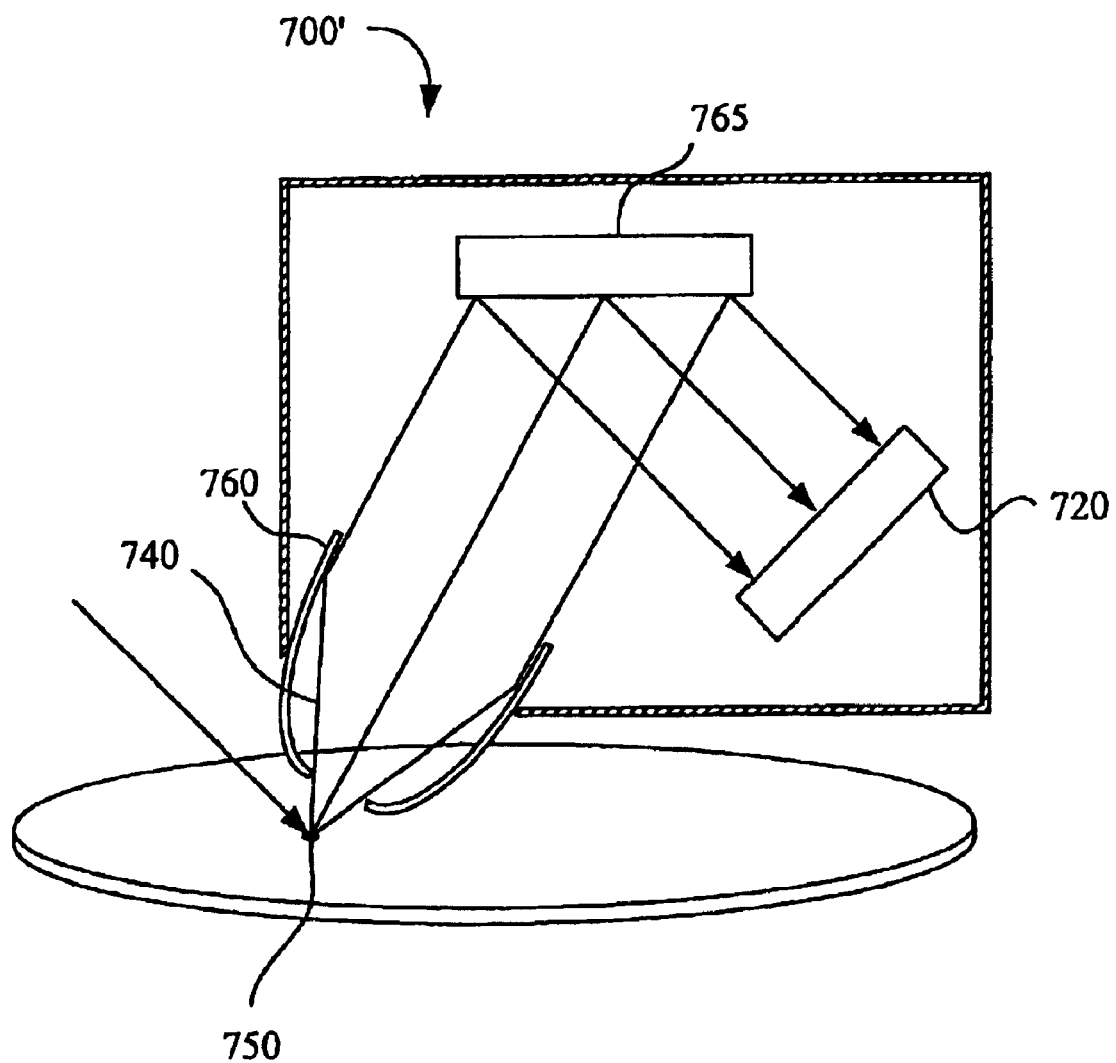
FIG. 8 is a cross-sectional view of a detector that can be used.

A cross-sectional view of an alternative embodiment of a WDS X-ray detector 700' is illustrated in FIG. 8. Detector 700' has a collimator 760 that captures the photons 740 emanating from the focus point 750, and then through its reflective surfaces causes the photons 740 to travel in substantially parallel paths. The collimator 760 is generally made from metal foil material. The photons then reflect off of a substantially flat reflective surface 765 such that the photons 740 continue in parallel paths towards the sensor 720. Similarly with detector 700, the reflective surface 765 in detector 700' may also be Bragg reflector or a crystal.

A common device which contains the general elements of the detector 700 and 700' is a Wavelength Dispersive System (WDS). By utilizing multiple WDS detectors, one or more photon peaks may be detected for each type of material that is expected to be present within the measured film stack of the specimen. That is, characteristic emission intensities for one or more types of material in the film stack may be measured. One or more individual detectors may also be dedicated to detect the various characteristic emission intensities for each type of material. For example, two WDS detectors may be dedicated for detecting two peaks associated with a copper material. As described earlier each material has different characteristic photons released due to an electron falling to each of the K, L, or M shells. By using multiple WDS detectors, the test system is able to obtain information for each of a multiple number of film layers.

Another type of detector, an Energy Dispersive System (EDS), collects photons in a wide spectrum of energies. EDS are capable of collecting a greater range of signals. As a result however, EDS detectors also collect photons having energies surrounding the characteristic photon energies. This causes EDS detectors to have lower signal to noise ratios.

The test system of the illustrated embodiment is capable of obtaining measurements having 0.5% precision with measurement times of 2 to 20 seconds. Thus, the test system allows for both accurate characterization and a high throughput rate.

Although the foregoing invention has been described in some detail for purposes of clarity of understanding, it will be apparent that certain changes and modifications may be practiced within the scope of the appended claims. The techniques of the present invention can be applied to measuring multiple layers of thin-films and determining the composition of thin films.

It should be noted that there are many alternative ways of implementing the techniques of the present invention. For example, prior to performing comparisons between x-ray emission measurements and control measurements, an entire wafer may be scanned and the corresponding emission measurements stored. The comparisons can then be performed after the entire wafer is scanned and the control measurement can be determined using emission measurements from the entire wafer. Accordingly, the present embodiments are to be considered as illustrative and not restrictive, and the invention is not to be limited to the details given herein, but may be modified within the scope and equivalents of the appended claims.

What is claimed is:

1. A method for characterizing thin films, the method comprising:
   scanning a first scan target in an integrated circuit device by using a particle beam generator configured to emit particles at a first energy, wherein the particles interact with a first layer comprising a first material and a second layer comprising a second material in the scan target, wherein the second layer lies beneath a first layer;
   detecting x-ray emissions associated with scanning at the first energy;
   scanning the first scan target by using the particle beam generator configured to emit particles at a second energy, the particles interacting with the first layer comprising the first material and the second layer comprising the second material in the scan target;
   detecting x-ray emissions associated with scanning at the second energy; and
   characterizing the second layer by using x-ray emissions from the first and second materials resulting from scans at the first and second energies.

2. The method of claim 1, wherein characterizing the second layer comprises determining the thickness of the second layer.

3. The method of claim 1, wherein characterizing the second layer comprises determining the composition of the second layer.

4. The method of claim 1, further comprising:
   characterizing the first layer.

5. The method of claim 4, wherein the first layer is a seed layer.

6. The method of claim 5, wherein the first layer comprises copper.

7. The method of claim 1, wherein the second layer is a barrier layer.

8. The method of claim 7, wherein the second layer comprises tantalum.

9. The method of claim 7, wherein the second layer comprises tantalum nitride.

10. The method of claim 1, wherein the first energy is determined using the expected thickness of the first and second layers.

11. The method of claim 1, wherein the second energy is determined using the first energy and the expected thickness of the first and second layers.

12. The method of claim 1, further comprising:
    scanning a reference material comprising the first material.

13. The method of claim 12, further comprising:
    scanning a reference material comprising the second material.

14. The method of claim 13, further comprising:
    determining K-ratios for the first and second materials for the first energy.

15. The method of claim 14, further comprising:
    determining K-ratios for the first and second materials for the second energy.

16. The method of claim 1, further comprising:
    scanning the first scan target by using the particle beam generator configured to emit particles at a third energy, the particles interacting with the first layer comprising the first material and the second layer comprising the second material in the scan target.

17. The method of claim 1, further comprising:
    continuously varying the particle beam energy between the first and second energies.

18. The method of claim 17, further comprising:
    detecting x-ray emissions resulting from a continuously varied particle beam energy.

19. The method of claim 1, wherein detecting x-ray emissions is performed by using a plurality of x-ray detectors.

20. The method of claim 19, wherein one or more x-ray detectors are tuned slightly away from characteristic x-ray energies to measure the background x-ray intensities at the first and second inducer energies.

21. An apparatus for measuring thin films, the apparatus comprising:
    an x-ray emission inducer operable to scan a first scan target in an integrated circuit device at a first energy and a second energy, wherein the x-ray emission inducer causes x-ray emissions from a first layer comprising a first material and a second layer comprising a second material in the scan target; and
    an x-ray emission detector operable to measure characteristic x-ray emissions resulting from the scan at the first energy and the second energy, wherein x-ray emissions characteristic of the first and second materials scanned at the first energy and the second energy are measured to characterize the second layer.

22. The apparatus of claim 21, wherein the x-ray emissions characteristic of the first and second materials are used to determine the thickness of the second layer.

23. The apparatus of claim 21, wherein the x-ray emissions characteristic of the first and second materials are used to determine the composition of the second layer.

24. The apparatus of claim 22, wherein the x-ray emission detector is further operable to characterize the first layer.

25. The apparatus of claim 24, wherein the x-ray emissions characteristic of the first and second materials are used to determine the thickness of the first layer.

26. The apparatus of claim 24, wherein the x-ray emissions characteristic of the first and second materials are used to determine the composition of the first layer.

27. The apparatus of claim 24, wherein the first layer is a seed layer.

28. The apparatus of claim 27, wherein the first layer comprises copper.

29. The apparatus of claim 21, wherein the second layer is a barrier layer.

30. The apparatus of claim 29, wherein the second layer comprises tantalum.

31. The apparatus of claim 29, wherein the second layer comprises tantalum nitride.

32. The apparatus of claim 21, wherein the first energy is determined based on the expected thickness the first and second layers.

33. The apparatus of claim 21, wherein the second energy is based on the expected thickness of the first and second layers.

34. The apparatus of claim 21, wherein the x-ray emissions characteristic of the first and second material are used to determined K-ratios for the first and second materials at the first and second energies.

35. The apparatus of claim 21, wherein the x-ray emission inducer is configured to continuously vary the energy of the scan between the first and second energies.

36. The apparatus of claim 35, wherein the x-ray emission detector is configured to detect emissions resulting from scans using continuously varying energies between the first and second energies.

37. The apparatus of claim 21, wherein additional x-ray emission detectors are tuned slightly away from characteristic x-ray energies to measure background x-ray intensities at the first and second inducer energies.

38. A method for measuring thin films, the method comprising:

scanning a first scan target in an integrated circuit device by using an x-ray emission inducer configured to scan at energies continuously varying between a first and a second energy, the scan target including a first layer comprising a first material and a second layer comprising a second material;

detecting x-ray emissions associated with scanning at energies continuously varying between the first and second energies, wherein x-ray emissions detected include emissions characteristic of the first and second materials used to determine the thickness and composition of the second layer.

39. The method of claim 38, wherein the x-ray emission detector is further operable to characterize the first layer.

40. The method of claim 39, wherein the x-ray emissions characteristic of the first and second materials are used to determine the thickness of the first layer.

41. The method of claim 39, wherein the x-ray emissions characteristic of the first and second materials are used to determine the composition of the first layer.

42. The method of claim 39, wherein the first layer is a seed layer.

43. The method of claim 42, wherein the first layer comprises copper.

44. The method of claim 38, wherein the second layer is a barrier layer.

45. The method of claim 44, wherein the second layer comprises tantalum.

46. The method of claim 44, wherein the second layer comprises tantalum nitride.

47. The method of claim 38, wherein the first energy is determined based on the expected thickness of the first and second layers.

48. The method of claim 38, wherein detecting x-ray emissions is performed by using a plurality of x-ray detectors.

49. The method of claim 48, wherein one or more x-ray detectors are tuned slightly away from characteristic x-ray energies to measure the background x-ray intensities at the first and second inducer energies.

* * * * *

UNITED STATES PATENT AND TRADEMARK OFFICE
CERTIFICATE OF CORRECTION

PATENT NO. : 6,788,760 B1
DATED : September 7, 2004
INVENTOR(S) : Janik et al.

It is certified that error appears in the above-identified patent and that said Letters Patent is hereby corrected as shown below:

Column 8,
Line 2, change "730 is having" to -- 730 having --.

Signed and Sealed this

Eighth Day of February, 2005

JON W. DUDAS
*Director of the United States Patent and Trademark Office*